United States Patent [19]
Scarfone et al.

[11] Patent Number: 5,300,046
[45] Date of Patent: Apr. 5, 1994

[54] THORACENTESIS SHEATH CATHETER ASSEMBLY

[75] Inventors: Frank A. Scarfone, Boca Raton; David H. Turkel, Miami, both of Fla.

[73] Assignee: Symbiosis Corporation, Miami, Fla.

[21] Appl. No.: 949,736

[22] Filed: Sep. 23, 1992

Related U.S. Application Data

[63] Continuation-in-part of Ser. No. 860,447, Mar. 30, 1992.

[51] Int. Cl.⁵ ............... A61M 5/00; A61M 25/00; A61M 5/178; A61M 5/14
[52] U.S. Cl. .................. 604/264; 604/169; 604/256; 251/149.8
[58] Field of Search ............. 604/31, 33, 110, 164, 604/167, 169, 246, 249, 256, 264; 251/149.8, 349

[56] References Cited

U.S. PATENT DOCUMENTS

| | | |
|---|---|---|
| 1,087,845 | 2/1914 | Stevens. |
| 1,103,967 | 7/1914 | Hughes. |
| 1,527,291 | 2/1925 | Zorraquin ............... 604/158 |
| 1,867,624 | 7/1932 | Hoffman. |
| 2,485,842 | 10/1949 | Pennington ............... 128/214 |
| 2,614,764 | 10/1952 | Annicq ............... 242/72 |
| 2,623,521 | 12/1952 | Shaw ............... 128/221 |
| 2,630,803 | 3/1953 | Baran ............... 128/221 |
| 2,842,124 | 7/1958 | James ............... 128/214 |
| 2,844,333 | 7/1958 | Davidson ............... 242/118.11 |
| 3,157,201 | 11/1964 | Littmann ............... 137/625.47 |
| 3,276,472 | 10/1966 | Jinkens et al. ............... 137/556 |
| 3,313,299 | 4/1967 | Spademan ............... 128/214.4 |
| 3,459,183 | 8/1969 | Ring et al. ............... 128/214.4 |
| 3,459,188 | 8/1969 | Roberts ............... 128/347 |
| 3,477,437 | 11/1969 | Goldberg ............... 128/347 |
| 3,530,492 | 9/1970 | Ferber ............... 128/221 |
| 3,542,026 | 11/1970 | Bledsoe ............... 604/247 |

(List continued on next page.)

FOREIGN PATENT DOCUMENTS

| | | |
|---|---|---|
| 0405883A3 | 1/1991 | European Pat. Off. ..... A61B 17/34 |
| 0232600B1 | 4/1991 | European Pat. Off. ..... A61M 1/00 |
| 575559 | 3/1923 | France. |
| 7535678 | 4/1975 | France ............... A61B 17/34 |
| 897224 | 1/1982 | U.S.S.R.. |

OTHER PUBLICATIONS

Vernay Custom Engineered Precision Rubber Components Catalog.
Surgical Laparoscopy, Ch. 2, pp. 40 & 41 by Talamini and Gadaez.
"Veress Needle in the Pleural Space," Southern Med. Journal vol. 76, No. 11, pp. 1383-1385 (Nov. 1983).

*Primary Examiner*—C. Fred Rosenbaum
*Assistant Examiner*—F. Wilkens
*Attorney, Agent, or Firm*—David P. Gordon

[57] ABSTRACT

A thoracentesis sheath catheter assembly includes a catheter connected to a valve body. The valve body is provided with a throughbore coaxial to the catheter for receiving a thoracentesis needle therethrough and a drainage bore in fluid communication with the first throughbore. The valve body is constructed as a first cylindrical portion which is connected to the catheter and a second cylindrical portion of larger inner diameter which is joined to the first cylindrical portion by a tapered inner wall. The second cylindrical portion contains a valve comprising a blocking ball and a spring biased plunger having a throughbore coaxial to the catheter, and is closed with a cap having a central hole and/or a gasket for sealingly receiving the thoracentesis needle. A thoracentesis needle extends through the hole of the cap, the gasket, the plunger, the first cylindrical portion and into and through the catheter. With the thoracentesis needle in place, communication between the throughbore and the drainage bore is blocked and a flow path is established through the needle. When the needle is removed, the throughbore is automatically obstructed by movement of the ball by the plunger along the tapered inner wall. However, a second fluid path is automatically established from the throughbore to the drainage bore.

17 Claims, 5 Drawing Sheets

U.S. PATENT DOCUMENTS

| | | | |
|---|---|---|---|
| 3,547,119 | 12/1970 | Hall et al. | 128/214.4 |
| 3,703,899 | 11/1972 | Calinog | 128/347 |
| 3,713,447 | 6/1973 | Adair | 128/347 |
| 3,727,613 | 4/1973 | Sorenson et al. | 128/214.4 |
| 3,765,420 | 10/1973 | Felczak | 128/347 |
| 3,774,604 | 11/1973 | Danielsson | 128/214.4 |
| 3,830,225 | 8/1974 | Shinnick | 128/2 B |
| 3,834,372 | 9/1974 | Turney | 128/2 F |
| 3,840,008 | 10/1974 | Noiles | 128/221 |
| 3,853,127 | 12/1974 | Spademan | 128/214.4 |
| 3,875,939 | 4/1975 | Mellor | 128/214.4 |
| 3,895,632 | 7/1975 | Plowiecki | 604/169 |
| 3,934,576 | 1/1976 | Danielsson | 128/2.05 D |
| 3,952,729 | 8/1976 | Libman et al. | 128/2 F |
| 3,977,400 | 8/1976 | Moorhead | 128/214.4 |
| 3,994,287 | 11/1976 | Turp et al. | 604/169 |
| 4,000,739 | 1/1977 | Stevens | 128/214.4 |
| 4,073,297 | 2/1978 | Kopp | 128/214.4 |
| 4,099,528 | 7/1978 | Sorenson et al. | 128/214.4 |
| 4,177,814 | 12/1979 | Knepshield et al. | 128/348 |
| 4,233,982 | 11/1980 | Bauer et al. | 604/169 |
| 4,245,635 | 1/1981 | Kontos | 604/169 |
| 4,252,122 | 2/1981 | Halvorsen | 128/349 R |
| 4,308,875 | 1/1982 | Young | 128/753 |
| 4,311,136 | 1/1982 | Weikl et al. | 604/110 |
| 4,314,565 | 2/1982 | Lee | 128/753 |
| 4,379,458 | 4/1983 | Bauer et al. | 604/264 |
| 4,403,617 | 9/1983 | Tretinyak | 128/754 |
| 4,447,235 | 5/1984 | Clarke | 604/169 |
| 4,496,348 | 1/1985 | Genese et al. | 604/169 X |
| 4,531,935 | 7/1985 | Berryessa | 604/45 |
| 4,535,773 | 8/1985 | Yoon | 604/51 |
| 4,540,411 | 9/1985 | Bodicky | 604/169 |
| 4,566,480 | 1/1986 | Parham | 137/271 |
| 4,626,245 | 12/1986 | Weinstein | 604/167 |
| 4,627,841 | 12/1986 | Dorr | 604/158 |
| 4,653,475 | 3/1987 | Seike et al. | 128/4 |
| 4,655,226 | 4/1987 | Lee | 128/754 |
| 4,700,694 | 10/1987 | Shishido | 128/6 |
| 4,735,215 | 8/1988 | Goto et al. | 128/754 |
| 4,745,950 | 5/1988 | Mathieu | 604/33 X |
| 4,784,156 | 11/1988 | Garg | 128/753 |
| 4,808,168 | 2/1989 | Warring | 604/158 |
| 4,832,044 | 5/1989 | Garg | 128/753 |
| 4,840,184 | 6/1989 | Garg | 128/753 |
| 4,844,087 | 7/1989 | Garg | 128/753 |
| 4,850,373 | 7/1989 | Zatloukal et al. | 128/749 |
| 4,850,973 | 7/1989 | Jordan et al. | 604/157 |
| 4,869,717 | 9/1989 | Adair | 604/51 |
| 4,887,998 | 12/1989 | Martin et al. | 604/110 |
| 4,891,044 | 1/1990 | Mitchell | 604/27 |
| 4,902,280 | 2/1990 | Lander | 604/165 |
| 4,907,599 | 3/1990 | Taylor | 128/754 |
| 4,917,668 | 4/1990 | Haindl | 604/169 X |
| 4,931,042 | 6/1990 | Holmes et al. | 604/164 |
| 4,973,312 | 11/1990 | Andrew | 604/158 |
| 5,036,860 | 8/1991 | Leigh et al. | 128/754 |
| 5,057,084 | 10/1991 | Ensminger et al. | 604/167 |
| 5,059,180 | 10/1991 | McLees | 604/110 |
| 5,078,688 | 1/1992 | Lobodzinski et al. | 604/164 |
| 5,098,388 | 3/1992 | Kulkashi et al. | 604/670 |
| 5,098,394 | 3/1992 | Luther | 604/167 |
| 5,104,381 | 4/1992 | Gresl et al. | 604/164 |
| 5,108,380 | 4/1992 | Herlitze et al. | 604/283 |
| 5,122,122 | 6/1992 | Allgood | 604/174 |
| 5,139,485 | 8/1992 | Smith et al. | 604/158 |

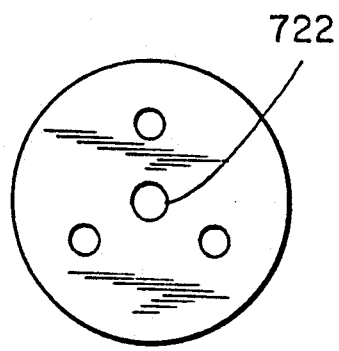
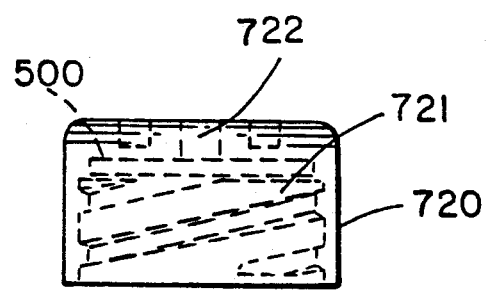
FIG. 7a          FIG. 7b
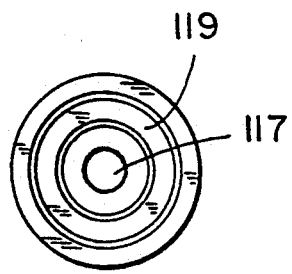
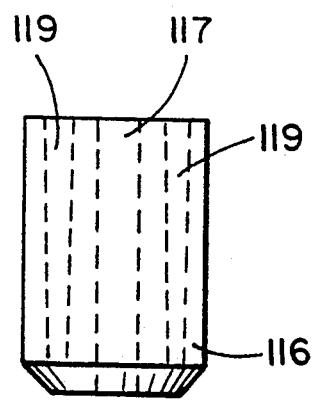
FIG. 8a          FIG. 8b

THORACENTESIS SHEATH CATHETER ASSEMBLY

This application is a continuation-in-part of U.S. Ser. No. 07/860,447, filed Mar. 30, 1992.

BACKGROUND OF THE INVENTION

The present invention generally relates to medical instruments. More particularly, the present invention relates thoracentesis needle devices which are used in the removal of fluid from the pleural cavity and which prevent air entry into the pleural cavity during use. Specifically, the invention relates to a sheath catheter assembly for a thoracentesis needle.

The thoracentesis procedure involves incising through the chest wall, and inserting a tube or catheter through the chest wall and into the pleural cavity. By providing a negative pressure at the proximal end of the catheter, intrathoracic fluid such as blood, puss, air, and other secretions are removed from the pleural cavity. While removal of the intrathoracic fluid is desirable, at the same time it is imperative for a negative pressure to be maintained in the pleural cavity in order to permit the lungs to remain expanded such that breathing can continue. In order to maintain a negative pressure in the pleural cavity, care must be taken to avoid communication between the pleural cavity and atmospheric pressure, as a passage of air from outside the body into the pleural cavity can collapse the lung; a medical condition known as pneumothorax.

A common manner of conducting a thoracentesis procedure is to make a chest wall incision using a needle. In introducing the needle into the pleural cavity, care must be taken to avoid pushing the needle too far and puncturing the lung, as air from the lung space could escape into the pleural cavity and result in a lung collapse. In such cases it is actually possible to produce a pressure within the pleural cavity which is greater than atmospheric pressure, and cardiac compromise is a possible consequence.

A thoracentesis device which purportedly reduces possibility of lung puncture and reduces pneumothorax due to entry of air into the pleural cavity is proposed in U.S. Pat. No. 4,447,235 to Clarke. The proposed device includes a needle having a drainage opening which extends through a catheter and through an elongated conduit connected to the catheter. The elongated conduit is provided with an elastomeric seal and a manual valve. The elastomeric seal, which is punctured by the needle when the needle ia inserted through the elongated conduit and catheter, prevents air leakage into the pleural cavity by sealing around the needle and resealing when the needle is removed. The manual valve, when moved, permits the elongate conduit to open to a side conduit when the needle is removed, thereby permitting long term drainage of the pleural cavity. In the Clarke patent, the removal of the needle is what reduces the possibility of lung puncture.

In addition to the device proposed in the Clarke patent, devices and procedures are set forth in U.S. Pat. Nos. 4,784,156, 4,832,044, 4,840,184, and 4,844,087 to Garg. In the Garg patents, a manual in-line valve is provided, and upon retraction of the needle past the valve, the valve is turned such that entry of air into the pleural cavity is prevented.

While the prior art patents represent advances in the art, it should be appreciated that with the prior art devices, it is still relatively easy for even a skilled surgeon to puncture the lung by pushing the needle just slightly too far into the pleural cavity. In fact, even if the needle is in the pleural cavity for a short period of time, should the patient move or cough, or even take a deep breath, it is possible for the needle to puncture the lung. In addition, with the manual valve structures of the prior art, should the attending surgeon forget to properly move the valve into the desired positions at certain times, undesirable results may be obtained.

Also long known in the art are needles called "Veress" or "Veress-type" needles. Veress needles are needles with an outer needle having a sharp distal end and an inner probe which extends through the outer needle with the probe having a blunt distal end. In Veress needles, the inner probe is biased to force the blunt distal end of the probe beyond the sharp distal end of the outer needle. However, when the blunt distal end of the probe encounters dense material, the probe is forced backward and the sharp end of the needle is presented so that it can puncture the dense material. Veress needles are used in the art almost exclusively for insufflation (injection of carbon dioxide) of the abdomen during laparoscopy procedures, and Veress needles with manual shut-off valves are known in the art. Veress needles have also been suggested for use in a thoracentesis procedure (See, Jenkins, Jr. Douglas, et al., "Veress Needle in the Pleural Space", *Southern Medical Journal*: Vol. 76, No. 11, pp. 1383-1395 (Nov. 1983)), although the techniques suggested therein in a test study have not gained popularity over the several years since they were reported and are not today used in common practice. Regardless of use, the Veress needle assemblies of the art have not before been modified for particular use in conjunction with withdrawal of fluid, and in particular withdrawal of fluid from the pleural cavity. Indeed, the Veress needle assemblies of the art have not been used with automatic check valves.

Parent application Ser. No. 07/860,447, discloses and claims a thoracentesis needle assembly which utilizes a Veress-type needle arrangement to overcome lung puncture problems as well as an automatic valve to prevent pneumothorax. In addition, the disclosed needle assembly may be used with a catheter such as the catheter disclosed by Clarke in U.S. Pat. No. 4,447,235. The catheter disclosed by Clarke, like the cannulae disclosed by Garg in U.S. Pat. Nos. 4,784,156, 4,832,044, 4,840,184, and 4,844,087, provides a manual valve in line with the needle assembly, and with a hollow cylindrical stopcock rotatably fitted with an external lever. Moving the external lever in one direction allows the thoracentesis needle to pass into the catheter, and moving the external lever in the other direction after the thoracentesis needle is removed prevents air from entering the catheter and directs fluid flow to a drainage attachment or the like. The chief disadvantages of the Clarke arrangement are that a valve which can be subject to clogging is used in the flow line, and that the in-line valve must be of exact design to permit needle insertion. Moreover, the attending surgeon must remember to set the valve to the correct position at the correct time. When the needle is inserted in the catheter, the valve must be placed in one position wherein the needle passes through the valve. After the needle is withdrawn from the catheter, the valve must be manually turned to a second position to redirect fluid flow from the catheter and block the needle passage. While Clarke provides an elastomeric seal in addition to the manual valve to prevent air from entering the catheter after the needle is withdrawn, this seal is merely a piece of elastomeric material which is pierced when the needle is inserted. Theoretically, when the needle is withdrawn, the elastomeric material will contract and close the opening which was made when the needle pierced it. While this solution sounds reasonable, it assumes that a needle of very small diameter is used. In practice, however, if a Veress-type needle is used, a piece of the elastomeric seal can be cut off by the needle and embedded inside the hollow of the needle. This presents two problems: first, a piece of elastomeric material will be delivered into the pleural cavity, and second, the resealing of the elastomeric seal is severely compromised since a piece of it is now missing.

SUMMARY OF THE INVENTION

It is therefore an object of the invention to provide a thoracentesis sheath catheter assembly which has an automatic valve means whereby the catheter is automatically sealed from the atmosphere and whereby the fluid path is automatically redirected to a drainage line when the thoracentesis needle is removed from the catheter.

It is another object of the invention to provide a thoracentesis sheath catheter assembly with a drainage line, where communication between the drainage line and the catheter is effectively closed when the thoracentesis needle is in the catheter.

It is a further object of the invention to provide a thoracentesis sheath catheter assembly with an automatic valve means wherein the catheter is automatically sealed and the fluid path is automatically redirected when the thoracentesis needle is removed from the catheter, and the thoracentesis needle is prevented from being reinserted into the catheter.

In accord with these objects, the thoracentesis sheath catheter assembly of the present invention generally comprises a catheter, and a valve assembly attached to the proximal end of the catheter. The valve assembly has a body having a throughbore coaxial to the catheter for receiving a thoracentesis needle, a side drainage port for coupling to a drainage line, and an automatic valve means distal the side drainage port for automatically sealing the throughbore when the needle is removed from the valve body.

Preferably, the valve body of the invention has a hollow first cylindrical portion, and a hollow tapered second cylindrical portion, with the first cylindrical portion having an internal diameter substantially the same as and coaxial to the internal diameter of the catheter and being attached to the proximal end of the catheter, and the tapered second cylindrical portion having an internal diameter larger than but coaxial to the internal diameter of the catheter and tapering down to the internal diameter of the first cylindrical portion. The tapered cylindrical portion contains the automatic valve. The automatic valve is preferably comprised of a blocking ball and a biased plunger, with the blocking ball having an external diameter larger than the internal diameter of the first cylindrical portion of the valve and being biased by the plunger towards the first cylindrical portion, and the plunger having a throughbore coaxial to the hollow tube to receive the thoracentesis needle. The internal diameter of the second cylindrical portion of the valve body is substantially the sum of twice the external diameter of the blocking ball plus the internal diameter of the first cylindrical portion such that the blocking ball is maintained in a position where it does not block communication between the first and second cylindrical portions when the thoracentesis needle is in place. Upon removal of the needle, the ball is pushed by the plunger down the taper to block the opening between the cylindrical portions; i.e., the flow path, and to prevent reinsertion of the needle. By preventing reinsertion of the needle, the assembly prevents the practitioner from accidentally piercing the catheter during a reinsertion procedure.

Additional objects and advantages of the invention will become apparent to those skilled in the art upon reference to the detailed description taken in conjunction with the provided figures.

BRIEF DESCRIPTION OF THE DRAWINGS

FIGS. 7a and 7b are top and side views of an alternative cap for use with the valve assembly of FIGS. 6a-6c.

FIGS. 8a and 8b are top and side views of a biased plunger used in the valve assemblies of the invention.

DETAILED DESCRIPTION OF THE PREFERRED EMBODIMENT

Figures 1, 2:
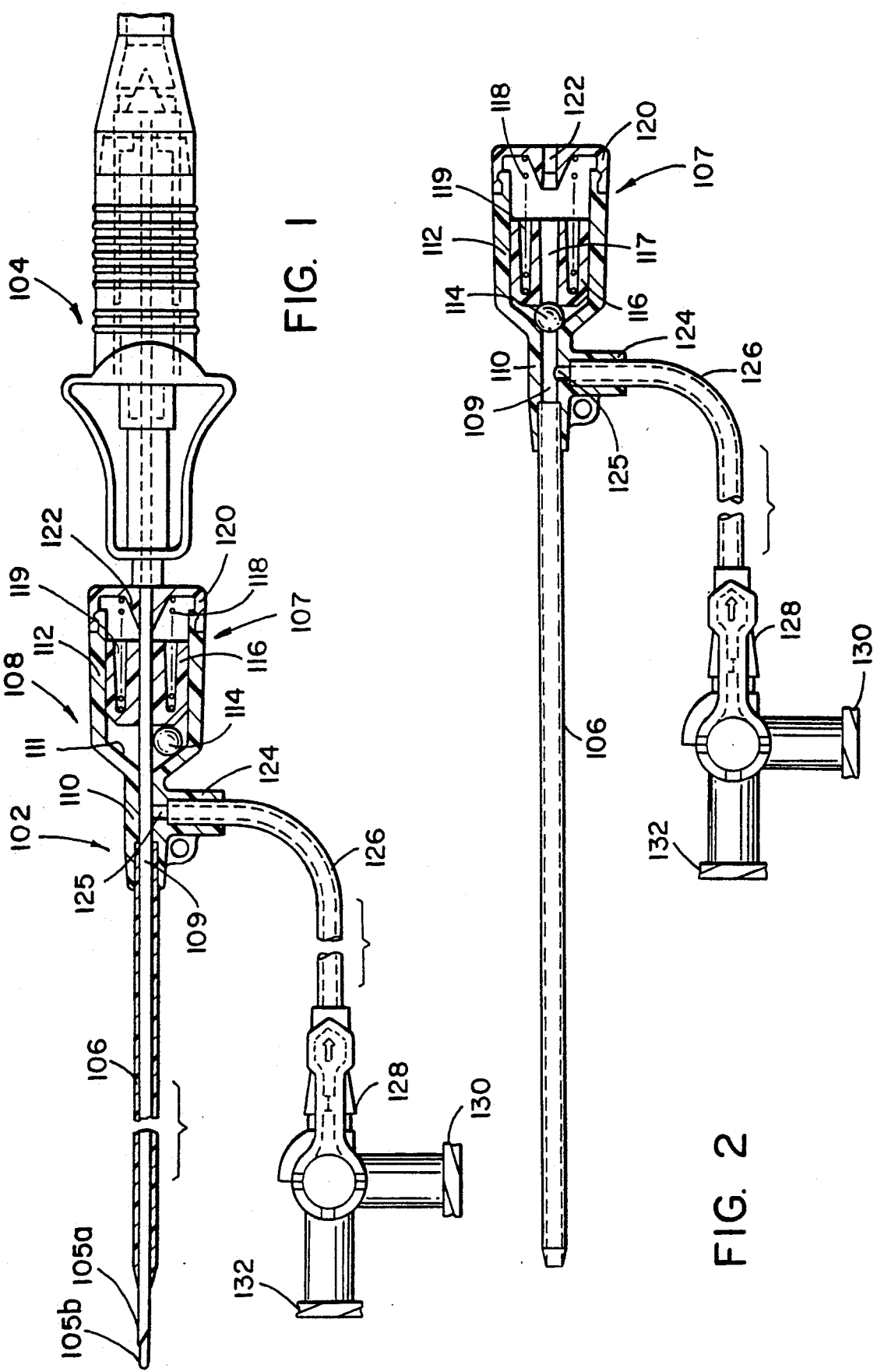
FIG. 1 is a side elevation view, partially in cross section of a thoracentesis sheath catheter assembly according to the invention with an attached drainage conduit and luer adapter, and a thoracentesis needle assembly inserted in the catheter.
FIG. 2 is a view similar to FIG. 1, but with the thoracentesis needle removed from the catheter.

Referring now to FIGS. 1-4, the preferred thoracentesis sheath catheter assembly 102 of the invention is shown, with a thoracentesis needle assembly 104 including needles 105a and 105b extending through the sheath catheter assembly and extending beyond the distal and proximal ends thereof. Details of the thoracentesis needle assembly 104 may be obtained with reference to parent application Ser. No. 07/860,447. The catheter assembly 102 of the invention includes a hollow tube or flexible catheter 106, and an automatic valve or flow control means 107 which includes a valve body 108 having a throughbore 109 which is in fluid communication with the proximal end of the catheter 106. The valve body 108 has a first cylindrical portion 110 which is connected to the proximal end of the catheter 106 and which has an internal diameter substantially the same as the internal diameter of catheter 106. The first cylindrical portion 110 is joined by a tapered inner wall 111 to a larger diametered second cylindrical portion 112. The second cylindrical portion 112 contains a blocking ball 114 and a biased plunger 116 which comprise part of the automatic valve or flow control means 107. The biased plunger 116 is provided with a coaxial throughbore 117, and is biased towards the ball 114 by a spring 118 which has a first end which sits in an annular recess 119 in the plunger 116 and a second end which rests against an end cap 120. The end cap is provided with a flexible or resilient throughbore 122 coaxial to the plunger throughbore 117.

As seen in FIGS. 1–4, the first cylindrical portion 110 of the valve body 108 is provided with a side drainage port and conduit connection 124 for receiving a draining conduit 126 (FIGS. 1 and 2). The draining conduit may be part of an assembly which includes a valve 128 with one or more luer adapters 130, 132 for connection to one or more bags (not shown). The drainage port 124 is in fluid communication with the throughbore 109 of the first cylindrical portion 110 of valve body 108 via opening 125.

Figure 3:
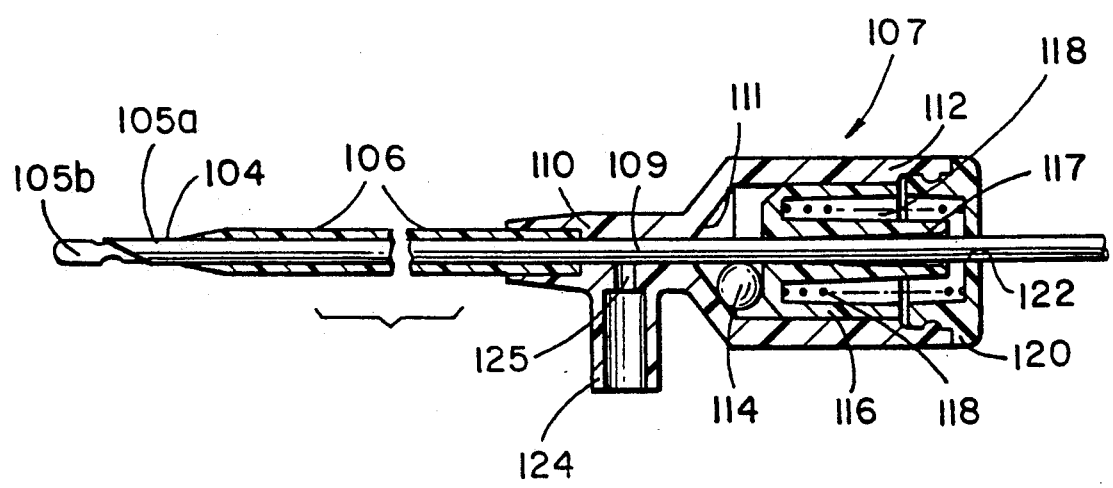
FIG. 3 is a cross sectional close up view of the valve portion of the catheter with a thoracentesis needle inserted.

As can be seen in FIGS. 1 and 3, when the needles 105a and 105b of the thoracentesis needle assembly 104 are in place in the catheter assembly 102, the blocking ball 114 is prevented from blocking throughbore 109 of the valve body 108 but remains biased against the tapered wall 111 by the plunger 116 and spring 118. Moreover, as long as outer needle 105a is in the catheter 106, fluid opening 125 is preferably effectively blocked and no communication between conduit connection 124 and throughbore 109 exists. Of course, even if fluid opening 125 were not totally blocked, positioning of valve 128 in a closed position would prevent fluid flow through opening 125 and port 124. Regardless, comparing FIGS. 2 and 4 to FIGS. 1 and 3, it can be seen that when the needle 105a is removed from the catheter assembly 102, fluid opening 125 is automatically opened and throughbore 109 is automatically closed. The closure of throughbore 109 is automatically obtained by the movement of the blocking ball 114 which is no longer impeded by the position of the needle 105a, but which is urged by the biased plunger 116 and spring 118 along the tapered wall 111 onto the throughbore 109. Because of the size of the ball and its biasing by the plunger and spring, the ball effectively seals the throughbore 109 so that communication with the hollow tube 106 is restricted to the drainage port 124. If valve 128 on draining conduit 126 is open, drainage through port 124 and into draining conduit 126 will also be automatic. Also, with the blocking ball 114 in place, reinsertion of the needles 105a, 105b into the catheter 106 is prevented.

Figure 4:
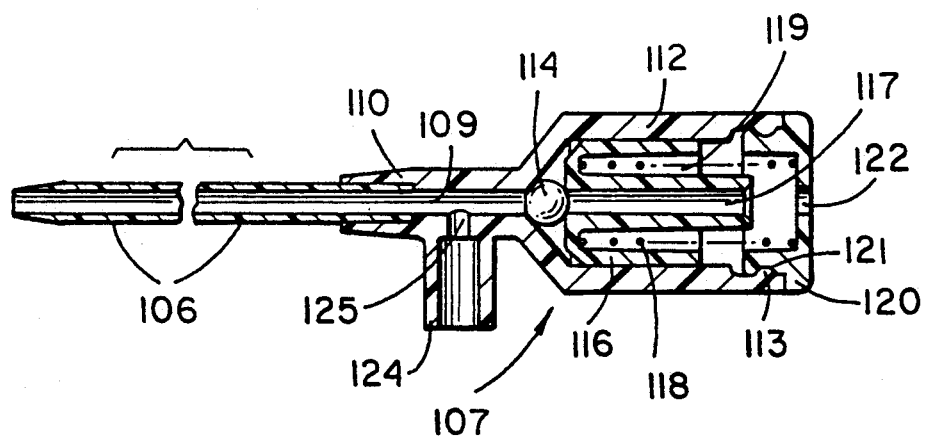
FIG. 4 is a view similar to FIG. 3 but with the thoracentesis needle removed.

It will also be appreciated that when needle 105a is removed from the catheter assembly 102 as shown in FIGS. 2 and 4, fluid communication between the side port 124 and the catheter 106 is effected prior to blocking ball 114 sealing throughbore 109. Those skilled in the art will appreciate further that a vacuum source attached to valve 128 and thereby to drainage port 124 enhances operation of the invention and achievement of the objects thereof.

Referring now to FIGS. 3 through 8, details of the valve body 108 and an alternate embodiment thereof, plunger 116, cap 120 and an alternative embodiment thereof, and a gasket 500, all of which are preferably used with the catheter assemblies are seen. As shown in FIGS. 3 and 4 and described above, the valve body 108 is provided with a cap 120 against which one end of spring 118 rests while biasing plunger 116. Cap 120 may take several forms such as a snap-on cap or a screw-on cap. A snap-on cap is shown in FIGS. 3 and 4 where the cap 120 is provided with an outer circumferential receiving groove 121 around which an engaging ridge 113 of the valve body 108 fits. In such an embodiment, either the cap 120 or the ridge 113 or both are constructed from a resilient material (e.g., plastic) such that the cap could be snapped into place and remain firmly attached to the valve body. As seen in FIGS. 3 and 4, the cap 120 fits inside the proximal end of the second cylindrical portion 112 of the valve body and extends around proximal end surface thereof.

A screw-on cap 720 is shown in FIGS. 7a and 7b. As seen in FIG. 7b, the screw-on cap 720 is provided with threads 721 which engage threads 613 of a modified valve body 108 shown in FIGS. 6a–6c. Preferably, once the cap 720 is threaded onto threads 613, the cap 720 is solvent bonded in place. In all embodiments of the cap, however, a central hole 122, (FIGS. 1–4), 722 (FIG. 6) is provided to receive the thoracentesis needle 104 (FIGS. 1 and 3). In accord with one embodiment of the invention, the cap material around the hole 122, 722 is elastomeric, and the hole 122, 722 is preferably sized so that when the thoracentesis needle 105a is in place in the catheter, the needle is closely gripped in the hole in an airtight sealing arrangement. By providing the hole, there is no concern that material will be broken off in the needle when the needle extends therethrough. At the same time, air still cannot enter the catheter. When the needle is removed from the catheter assembly and the hoe 122, 722 is exposed, The ball valve acts to prevent air from entering the catheter.

Figure 5:
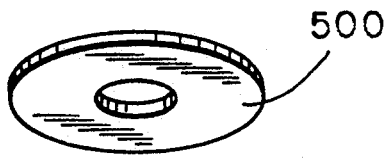
FIG. 5 is a perspective view of an elastomeric sealing gasket for use in conjunction with the valve portion of the catheter assembly shown in FIGS. 3 and 4.
Figure 6A:
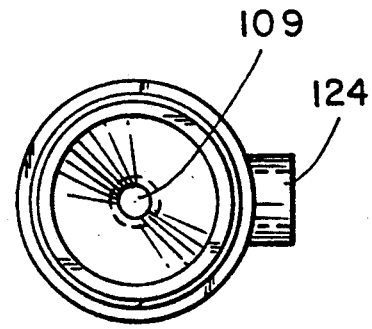
FIGS. 6a, 6b, and 6c are respectively top, side, and bottom views of a second embodiment of the valve assembly of the invention.
Figure 6B:
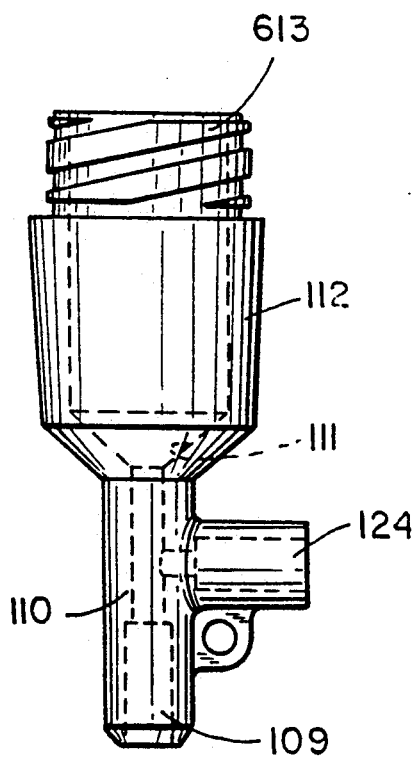
Figure 6C:
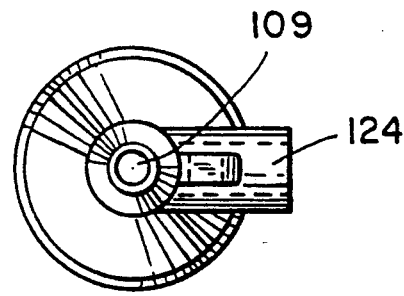

According to another preferred embodiment of the invention, instead of providing a cap with an elastomeric hole 122, 722, an elastomeric sealing gasket 500 as seen in FIG. 5 is used. The outer diameter of the elastomeric sealing gasket 500 is preferably chosen so that the sealing gasket establishes a frictional engagement with the internal proximal end of the cap 120, 720 Also, the internal hole of the gasket 500 is sized to grip the thoracentesis needle 105a in an airtight sealing arrangement. The sealing gasket 500 is held in place both by its friction fit in the cap (as shown in phantom in FIG. 7b), as well as by spring 118 Which seals against the gasket 500, although the spring 118 is sufficient by itself. By providing a sealing gasket 500, the caps 120, 720 are simplified, as the material around holes 122, 722 therein need not be made of an elastomeric material, and the holes 122, 722 need not be sized exactly.

Turning to FIGS. 8a and 8b, details of the plunger 116 are more clearly seen. As previously described, the plunger 116, in addition to having a central throughbore 117, is also provided with a recess or annulus 119 for coaxially receiving and securely engaging spring 118.

According to another aspect of the invention, in order to establish a more effective seal of throughbore 109, a flexible opening between portions 110 and 112 of the valve body is provided into which the ball 114 seats. In particular, and with reference to FIG. 9a, a sheath 197a of flexible material such a plastic which is softer than the valve body is preferably insert molded into the valve body at a location between the termination of tapered wall 111 and cylindrical portion 110. Because the sheath 197a is relatively soft, when the ball 114 is pushed by plunger 116 down ramp 111 and into a position to close throughbore 109, the force of the spring loaded plunger 116 causes the ball to resiliently deform the sheath 197a and make a good seal therewith.

Figure 9C:
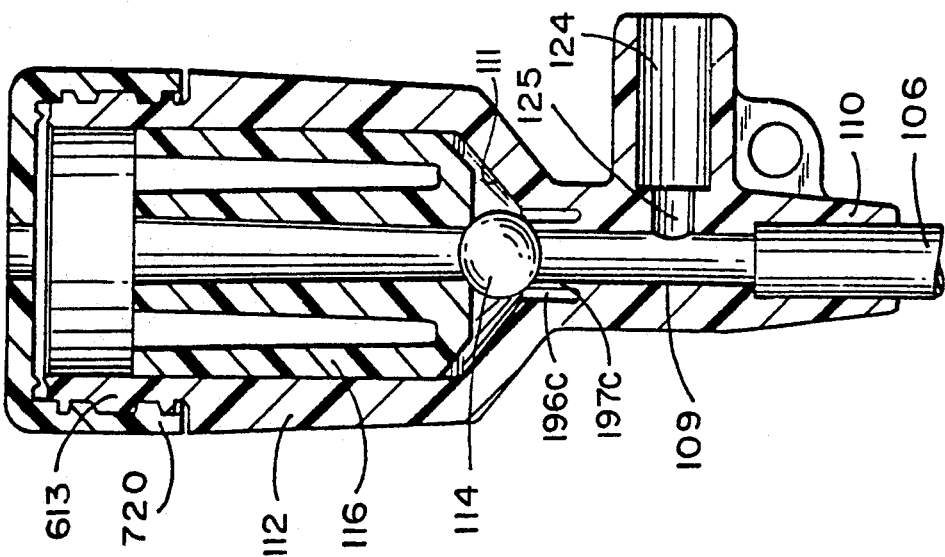
FIGS. 9a, 9b, and 9c are cross sectional views of three alternative embodiments of the valve body of the catheter assembly where different means are utilized to provide a flexible opening between portions of the valve body.
Figure 9B:
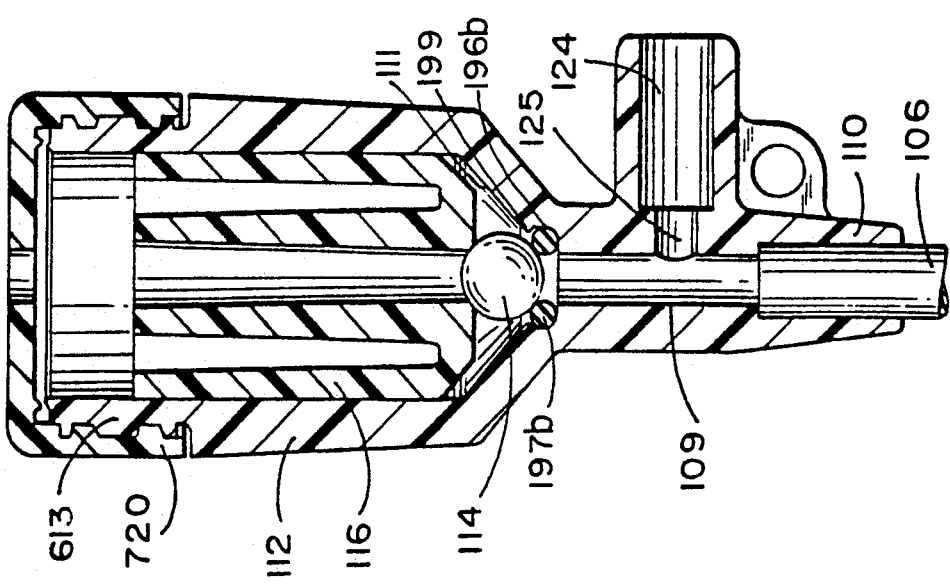
Figure 9A:
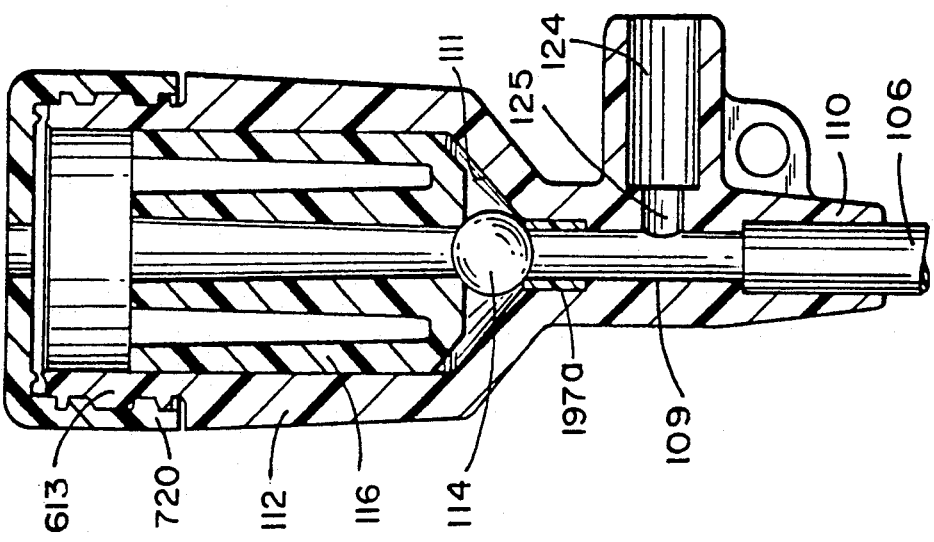

Two additional mechanisms for accomplishing the flexible opening are seen in FIGS. 9b and 9c. In FIG. 9b, an O-ring 197b is provided in a seat 196b which is provided between the tapered wall 11 and the throughbore 109 of cylindrical portion 110. Preferably, a small annular protrusion 199 is provided in the seat such that the O-ring is pushed past the protrusion and snaps into place in the seat 196b. With the O-ring in place, when the ball 114 is pushed by plunger 116 down ramp 111 and into a position to close the throughbore 109, the force of the spring loaded plunger 116 causes the ball to resiliently deform the O-ring 197b and make a good seal therewith.

Turning to FIG. 9c, it is seen that the valve body is molded with a radial channel or annulus 196c. Together with throughbore 109, the annulus 196c defines a thin cylinder 197c, which, because of its thin wall is flexible. Thus, when ball 114 is pushed by plunger 116 down ramp 111 and into a position to close the throughbore 109, the force of the spring loaded plunger 116 causes the ball to resiliently deform the wall of cylinder 197c and make a good seal therewith.

It is intended that the catheter of the invention be packaged with the thoracentesis needle inserted in it so that it is ready for use by the surgeon. Preferably, in assembly, the needles 105a, 105b of the thoracentesis needle assembly 114 are first inserted through the hole 122, 722 in an unassembled end cap 120, 720, then through the gasket 500 (if any), then through throughbore 117 of an unassembled plunger (with spring 118 in place), and then through the throughbore 109 of a valve body 108 which may have ball 114 already contained in the second cylindrical portion 112. If the ball 114 is already in the valve body, it is moved aside in order for the needle assembly 114 to be inserted through throughbore 117. If the ball 114 is not in the valve body upon insertion of the needles, with the needles in place, the ball 114 is placed into the second cylindrical portion 112 of valve body 108. The end cap 120, 720 (with gasket 500 in place if used) is then pushed distally to engage the spring 118 and then to engage the valve body (either by snapping it thereon, or by screwing it thereon), so as to capture the plunger 116 and spring 118 in the second cylindrical portion 112 and obtain the arrangement shown in FIGS. 1 and 3. Prior to assembly, the catheter 106 is insert molded and drainage line 126 is preferably bonded to the valve body 108.

There have been described and illustrated herein several embodiments of a thoracentesis sheath catheter assembly. While particular embodiments of the invention have been described, it i not intended that the invention be limited thereto, as it is intended that the invention be as broad in scope as the art will allow and that the specification be read likewise. Thus, while particular caps and a particular ball valve have been disclosed, it will be appreciated that other types of caps and flow control mechanisms could be utilized provided that a seal is always maintained to prevent leakage of air into the catheter, and provided that the flow control mechanism is automatic so that removal of the needle automatically changes the flow path to the drainage port. Also, while the valve body has been described as having cylindrical portions, it will be recognized that other shaped valve bodies, and valve bodies having a different number of portions could be utilized. Moreover, while particular configurations have been disclosed in reference to the conduit connection as part of the valve body, it will be appreciated that other configurations of the conduit connection apart from the valve body could be used as well. Likewise, while particular configurations for providing a flexible opening between the different cylindrical portions of the valve body were disclosed to provide a good seal, it will be appreciated that other arrangements could be utilized. In fact, if desired, the ball utilized can be sufficiently elastic such that the ball deforms into the opening, and the opening need not be elastic. It will therefore be appreciated by those skilled in the art that yet other modifications could be made to the provided invention without deviating from its spirit and scope as so claimed.

What is claimed is:

1. A thoracentesis sheath catheter assembly adapted for use with a thoracentesis needle assembly having a needle, comprising:
   a) a hollow catheter means having a proximal end, a distal end, and a longitudinal axis; and
   b) a valve means having a valve body and a flow control means,
      said valve body having a distal end coupled to said proximal end of said hollow catheter means, a first throughbore substantially parallel to said longitudinal axis and in fluid communication with said hollow catheter means, said first throughbore sized to receive the needle therein and to allow the needle to pass through said first throughbore and through said hollow catheter means to form a first flow path through the needle in said first throughbore,
      said valve body having a second bore in fluid communication with said first throughbore, said second bore being located distally relative to said flow control means,
      said valve body having a hollow portion proximal said second bore, said hollow portion having a tapered inner wall section which tapers as it extends distally, and with said hollow portion terminating in said first throughbore, and
      said flow control means including a ball and biasing means for biasing said ball towards said distal end of said catheter means, wherein said ball and biasing means are held in said hollow portion of said valve body,
      wherein as the needle is removed from said first throughbore, said biasing means automatically biases said ball along said tapered wall and blocks said first throughbore, thereby preventing a flow path from forming through and out said first throughbore, and causing a second flow path to be formed from said hollow catheter, into said first throughbore, and into and out said second bore.

2. A thoracentesis sheath catheter assembly according to claim 1, further comprising:
   drainage port tube means coupled to sad second bore of said valve body.

3. A thoracentesis sheath catheter assembly according to claim 2, wherein:
   said second bore is substantially perpendicular to said first throughbore, and an opening between said second bore and said first throughbore is substantially closed when the needle is located in said first throughbore.

4. A thoracentesis sheath catheter assembly according to claim 1, further comprising:
   end cap means for covering a proximal end of said valve body, said end cap means having a resilient portion with a hole therein, said hole sized to receive the needle in an airtight sealing engagement.

5. A thoracentesis sheath catheter assembly according to claim 1, further comprising:
end cap means for covering a proximal end of said valve body, said end cap means having a hole therein, and
an elastomeric sealing gasket sized to fit in said end cap means, and having a center hole sized to receive the needle in an airtight sealing engagement.

6. A thoracentesis sheath catheter assembly according to claim 4, further comprising:
drainage port tube means coupled to said second bore of said valve body, wherein said second bore is substantially perpendicular to said first throughbore.

7. A thoracentesis sheath catheter assembly according to claim 5, further comprising;
drainage port tube means coupled to sad second bore of said valve body, wherein said second bore is substantially perpendicular to said first throughbore.

8. A thoracentesis sheath catheter assembly according to claim 1, wherein:
said biasing means comprises plunger means and spring means inside said hollow portion, said spring means for biasing said plunger means towards said tapered inner wall, and said plunger means having a second throughbore for receiving the needle.

9. A thoracentesis sheath catheter assembly according to claim 4, wherein:
said biasing means comprises plunger means and spring means inside said hollow portion, said spring means for biasing said plunger means towards said tapered inner wall, and said plunger means having a second throughbore for receiving the needle.

10. A thoracentesis sheath catheter assembly according to claim 5, wherein:
said biasing means comprises plunger means and spring means inside said hollow portion, said spring means for biasing said plunger means towards said tapered inner wall, and said plunger means having a second throughbore for receiving the needle.

11. A thoracentesis sheath catheter assembly according to claim 1, wherein:
said hollow portion has a first cylindrical portion attached to said catheter and a second cylindrical portion proximal said first cylindrical portion, said first and second cylindrical portions having respective first and second inner diameters, said second inner diameter being larger than said first inner diameter, said second cylindrical portion being joined to said first cylindrical portion by said tapered inner wall, and
said ball and said biasing means both located inside said second cylindrical portion, said ball having an outer diameter larger than said first inner diameter and smaller than said second inner diameter, and said biasing means for biasing said ball towards said first cylindrical portion.

12. A thoracentesis sheath catheter assembly according to claim 3, wherein:
said biasing means comprises spring means and plunger means both inside said second cylindrical portion, said plunger means having a second outer diameter smaller than said second inner diameter but larger than said first outer diameter, and said plunger means having a second throughbore, said second throughbore having an inner diameter substantially the same size as and coaxial to said first inner diameter, wherein said spring means biases said plunger means towards said tapered inner wall.

13. A thoraoentesis sheath catheter assembly according to claim 1, further comprising:
resilient means in said valve body for receiving said ball and sealingly mating therewith to block said first throughbore, said resilient means being located between a termination of said tapered inner wall section and said first throughbore.

14. A thoracentesis sheath catheter assembly according to claim 13, wherein:
said resilient means comprises one of a resilient sheath, an O-ring, and a thin cylinder.

15. A thoracentesis sheath catheter assembly according to claim 12, further comprising:
end cap means for covering a proximal end of said valve body said end cap means having a resilient portion with a hole therein, said hole sized to receive the needle in an airtight sealing engagement.

16. A thoracentesis sheath catheter assembly according to claim 12, further comprising:
end cap means for covering a proximal end of said valve body said end cap means having a hole therein, and
an elastomeric sealing gasket sized to fit in said end cap means, and having a center hole sized to receive the needle in an airtight sealing engagement.

17. A method of draining fluid from a thoracic cavity, utilizing a thoracentesis sheath assembly and a thoracentesis needle assembly, where the thoracentesis needle assembly has a needle, and the thoracentesis sheath assembly has a hollow catheter means having a proximal end, a distal end, and a longitudinal axis, and a valve means having a valve body and a flow control means, with said valve body having a distal end coupled to said proximal end of said hollow catheter means, and said valve body has a first throughbore substantially parallel to said longitudinal axis and in fluid communication with said hollow catheter means, said first throughbore being sized to receive the needle therein and to allow the needle to pass through said first throughbore and through said hollow catheter means to form a first flow path through the needle in said first throughbore, and said valve body having a second bore in fluid communication with said first throughbore, said second bore being located distally relative to said flow control means, said valve body having a hollow portion proximal said second bore, said hollow portion having a tapered inner wall section which tapers as it extends distally, and with said hollow portion terminating in said first throughbore, and said flow control means including a ball and biasing means for biasing said ball towards said distal end of said catheter means, wherein said ball and biasing means are held in said hollow portion of said valve body, said method comprising:
a) with said needle and said hollow catheter means in the thoracic cavity, with the needle extending through said hollow catheter means, removing said needle from said first throughbore, whereby said biasing means automatically biases said ball along said tapered wall and blocks said first throughbore, thereby preventing a flow path from forming through and out said first throughbore, and causing a second flow path to be formed from said hollow catheter, into said first throughbore, and into and out said second bore; and
b) draining said fluid through said second flow path.

* * * * *